United States Patent [19]

Hill

[11] 4,120,295

[45] Oct. 17, 1978

[54] APPARATUS FOR INTEGRATION OF FLUID DILUTION CURVES

[76] Inventor: Thomas A. Hill, 2645 NW. 26th, Oklahoma City, Okla. 73107

[21] Appl. No.: 750,278

[22] Filed: Dec. 13, 1976

[51] Int. Cl.² .............................................. A61B 5/02
[52] U.S. Cl. .............................. 128/2.05 F; 73/194 E; 307/229; 328/127; 364/416; 364/510
[58] Field of Search ..................... 128/2.05 F, 2.05 R, 128/2.05 V; 73/194 F, 204; 235/183; 307/229; 328/127; 364/416, 510, 811, 829, 834

[56] References Cited

U.S. PATENT DOCUMENTS

| | | | |
|---|---|---|---|
| 3,269,386 | 8/1966 | Sherman | 128/2.05 F X |
| 3,304,413 | 2/1967 | Lehmann et al. | 128/2.05 F X |
| 3,433,935 | 3/1969 | Sherman | 128/2.05 F X |
| 3,553,723 | 1/1971 | Ohnsorg | 235/183 X |
| 3,651,318 | 3/1972 | Czekajewski | 128/2.05 F X |
| 3,678,922 | 7/1972 | Phillips et al. | 128/2.05 F |
| 3,679,880 | 7/1972 | Carver | 235/183 X |
| 3,859,602 | 1/1975 | Janssen et al. | 128/2.05 F X |
| 3,875,428 | 4/1975 | LeBlanc | 307/229 |
| 4,001,698 | 1/1977 | Allred | 328/127 X |
| 4,015,593 | 4/1977 | Elings et al. | 128/2.05 F X |

*Primary Examiner*—Lee S. Cohen
*Attorney, Agent, or Firm*—Robert M. Hessin

[57] ABSTRACT

A method for obtaining integral data of the dilution curve obtained when an indicator is injected into a closed system containing a circulating fluid, and as particularly adapted for utilization in blood flow analysis computers. The apparatus is constructed to analyze the characteristic concentration curve in an abbreviated time period to establish the full integral value of the curve. Concentration curve input is integrated through circuitry which detects relative curve change through a Phase I for subsequent summation with a data value summation through a selected portion of the exponential decay curve, that portion identified as Phase II, thereby to predict the remainder of the curve area and provide data output of an integral value for the entire concentration curve above a designated zero or set point level.

6 Claims, 3 Drawing Figures

APPARATUS FOR INTEGRATION OF FLUID DILUTION CURVES

BACKGROUND OF THE INVENTION

1. Field of the Invention

The invention relates generally to geometric curve integrating apparatus and, more particularly, but not by way of limitation, it relates to an improved method and apparatus for deriving data values relating to a blood system concentration curve which is indicative of blood flow rate and heart pumping efficiency.

2. Description of the Prior Art

The prior art has seen many attempts at both method and apparatus of effectively deriving usable data indications which relate to the concentration curve of the blood circulatory system. Initially, such integrations were taken by the conventional means utilizing a simple timer which was employed to time the integration of the concentration curve for a preset duration. The timing of such integration was necessarily established by a trial and error system and was subject to error due to variation in reference level. Still other approaches have been utilized wherein the concentration curve peak value was measured and remaining additive values derived therefrom were summed to obtain a final value. Of particular interest is the Czekajewski Pat. No. 3,651,318 which teaches an analog form of computer which functions to establish a concentration curve peak value that is then utilized to construct a subsequent exponential curve portion response approximating the actual concentration curve integral value. Still other forms of analog approximation device as well as digital devices have been utilized in previous attempts to solve the problem of obtaining reliable concentration curve integrals consonant with the requirements and standards of human body testing devices.

SUMMARY OF THE INVENTION

The present invention contemplates apparatus for analysis of blood concentration data as utilized in circulatory system test analysis computers. The invention consists of detection comparator and logic circuitry for deriving a time analog output signal indicative of the total integral value of a blood dilution concentration curve of the well-known characteristic shape.

Therefore, it is an object of the present invention to provide an improved concentration analyzer of the analog type which provides a reliable integral output through prediction of the later exponential portion of the characteristic curve.

It is also an object of the invention to provide an apparatus which is relatively simple yet capable of stabilization to provide continual reliable readouts of the blood flow data.

Finally, it is an object of the present invention to provide an apparatus for providing a time analog blood flow rate output indication for further processing through either digital or analog circuitry to provide various blood analysis functions.

Other objects and advantages of the invention will be evident from the following detailed description when read in conjunction with the accompanying drawings which illustrate the invention.

DETAILED DESCRIPTION OF THE INVENTION

Figure 1:
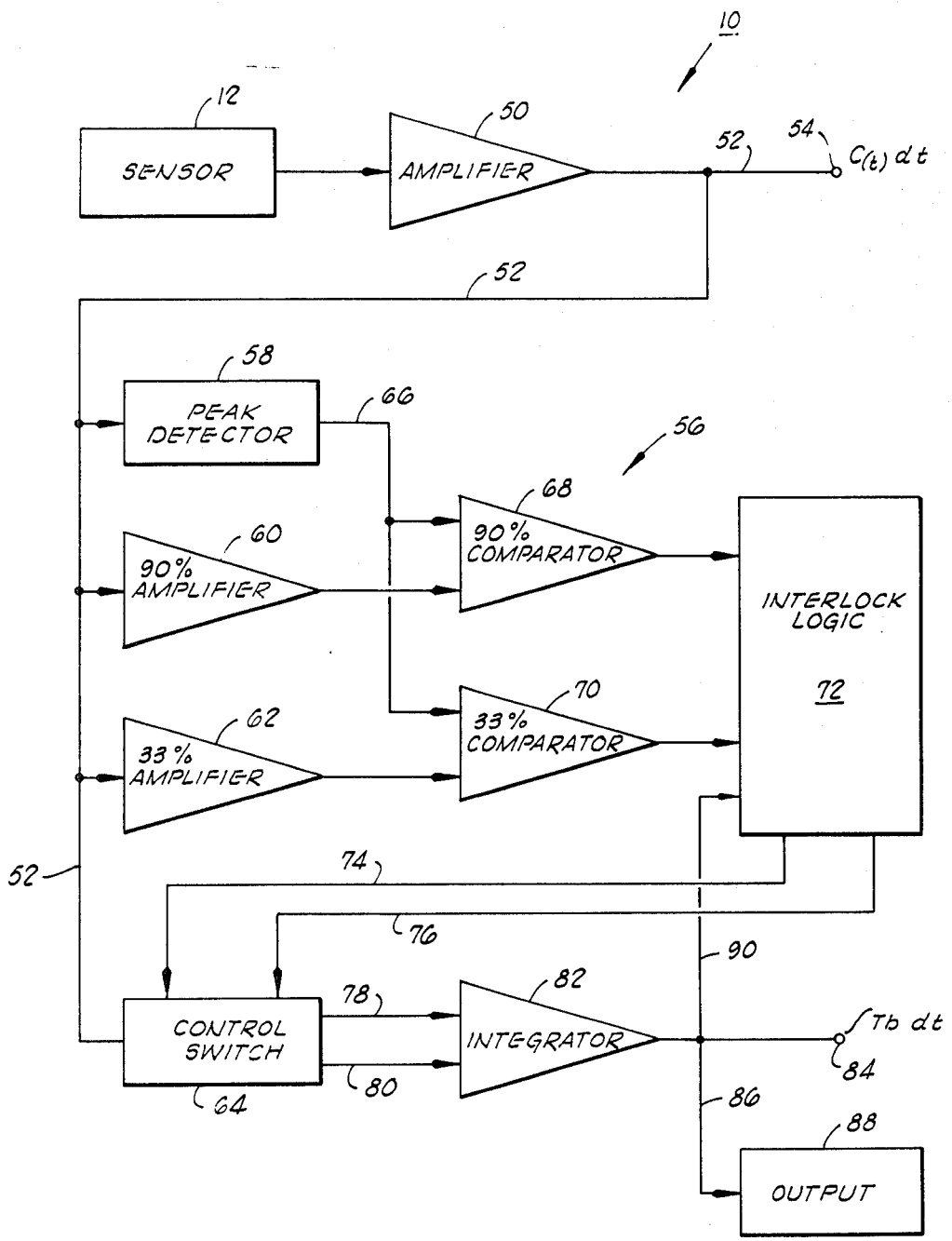
FIG. 1 is a block diagram of the concentration curve analysis circuit of the present invention.

FIG. 1 illustrates a block diagram of an integral portion of a blood analysis computer, that portion which is utilized for the blood flow determination through sensing of a blood concentration curve and subsequent integration and prediction to obtain an output data value. The circuit 10 is utilized to obtain data for use in solution of the standard Stewart-Hamilton indicator dilution equation which provides $$\text{Flow Rate (Liters/min)} = K \frac{V \Delta C}{\int_0^\infty C dt} \quad (1)$$

where $V$ is indicator volume and $C$ is equal to concentration.

Blood flow measurement, or the concentration curve input $C(t)_{dt}$, is a quantity which is presently measured by any of several methods which include thermal convection wherein rate of cooling a warm object in a colder-flowing medium is sensed; or, the concentration may be measured by radiographic methods which sense time distribution of a radio isotope through the blood system; or, concentration may be measured utilizing distribution of a dye indicator such as cardiogreen dye injected in the circulatory system and sensed to provide time analog output indication. While circuit 10 of FIG. 1 may be utilized with any of such sensing methods, the following will be described in relation to temperature T sensing wherein such as normal saline solutions or 5 percent dextrose solution at pre-set temperature is injected into the right atrium and thereafter sensed or measured by placement of a thermistor in the pulmonary artery. Thus, sensor 12 would constitute the thermistor and related positioning and conducting structure which is well-known in the technology.

Figure 2:
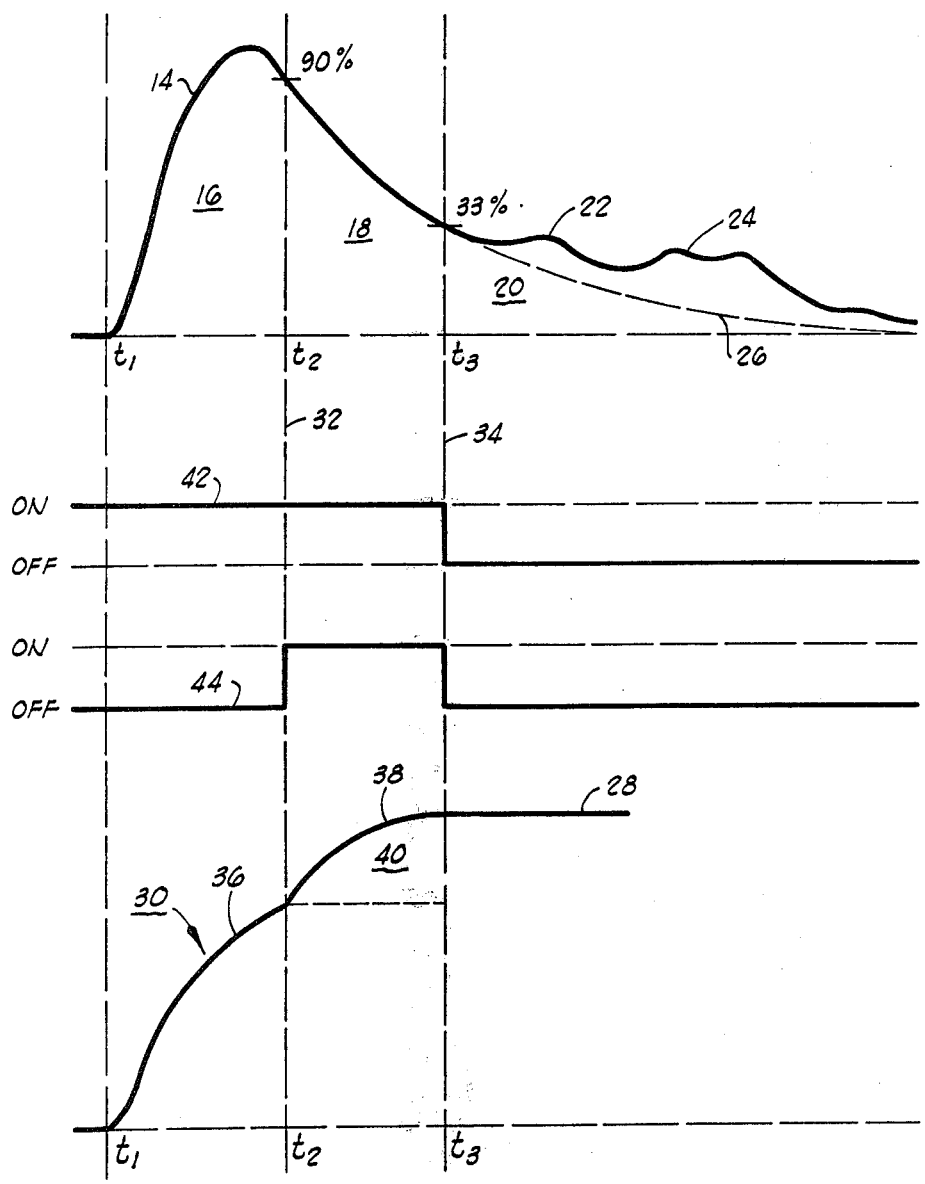
FIG. 2 is a time analog graph which depicts in synchronism each of the concentration curves, the integral value, and control switch sequencing.

The circuit 10 functions to determine the total time integral value beneath the concentration curve as shown in the graphic depiction of FIG. 2. The concentration curve for input $C(t)_{dt}$ is shown by curve 14 and includes a Phase I portion 16, due to injection of the indicator into the closed blood system; a Phase II portion 18, selected as 90% to 33% of decay, during which true exponential decay is sensed; and a Phase III portion 20, during which a recirculation hump 22 as well as noise and other unreliable return 24 may be sensed thereby to deviate from the true exponential decay to infinity, as shown by dash line 26. The integral concentration data value sought is indicated by line 28 of the integral curve 30 shown in synchronous relationship therebelow. The present method of determination acts upon phases 16 and 18 of concentration curve 14, as delineated by time switching shown at dash lines 32 and 34, in order to determine the Phase I integral value 36 for summation with a Phase II integral value 38. Integral value 38 includes a predicted value, or portion 40, which is equal to the exponentially tailing part of curve portion 20 which is unreliably affected by recirculation hump 22 and noise, scatter and the like 24. Thus, a distinct cut-off processing time is made at the time line 34, whereupon data readout and further calculation or computation is effected, and the system may be re-set for next reading usage. Graphic lines 42 and 44 represent integration control switching sequences as will be further described below.

Referring again to FIG. 1, the sensor 12 indicating blood concentration variations in response to an induced dilution provides output to amplifier 50 which, in turn, provides an output analog value of the concentration for $C(t)_{dt}$ on a lead 52. The output terminal 54 provides the concentration output for applications to other portions of the blood analysis system which constitute no part of the present invention, while remainder lead 52 provides inputs to the integration circuitry 56. Thus, the concentration signal on lead 52 is applied in parallel to each of peak detector 58, a 90 percent amplifier 60, a 33 percent amplifier 62, and a dual mode control switch 64. Peak detector 58 then provides output on a lead 66 to provide peak value signal in parallel to each of a 90 percent comparator 68 and a 33 percent comparator 70 which generate output signals in response to input of respective 90 percent amplifier 60 and 33 percent amplifier 62 for energization of the interlock logic 72.

Output from interlock logic 72, as will be further described in detail, is via leads 74 and 76 to control switch 64, as controlled in accordance with the sequencing of lines 42 and 44 of FIG. 2, to provide selected outputs on leads 78 and 80 for integration in an integrator 82 to provide output of the integral data value at terminal 84. Terminal 84 provides the output temperature T integral value for conduction and usage in other components of the blood analysis system, while the output lead 86 may be applied to a direct readout meter or recording structure of a type well-known in the art, shown generally as output 88. The parallel lead 90 applies the integral output back to interlock logic 72 in a manner as will be described below.

Figure 3:
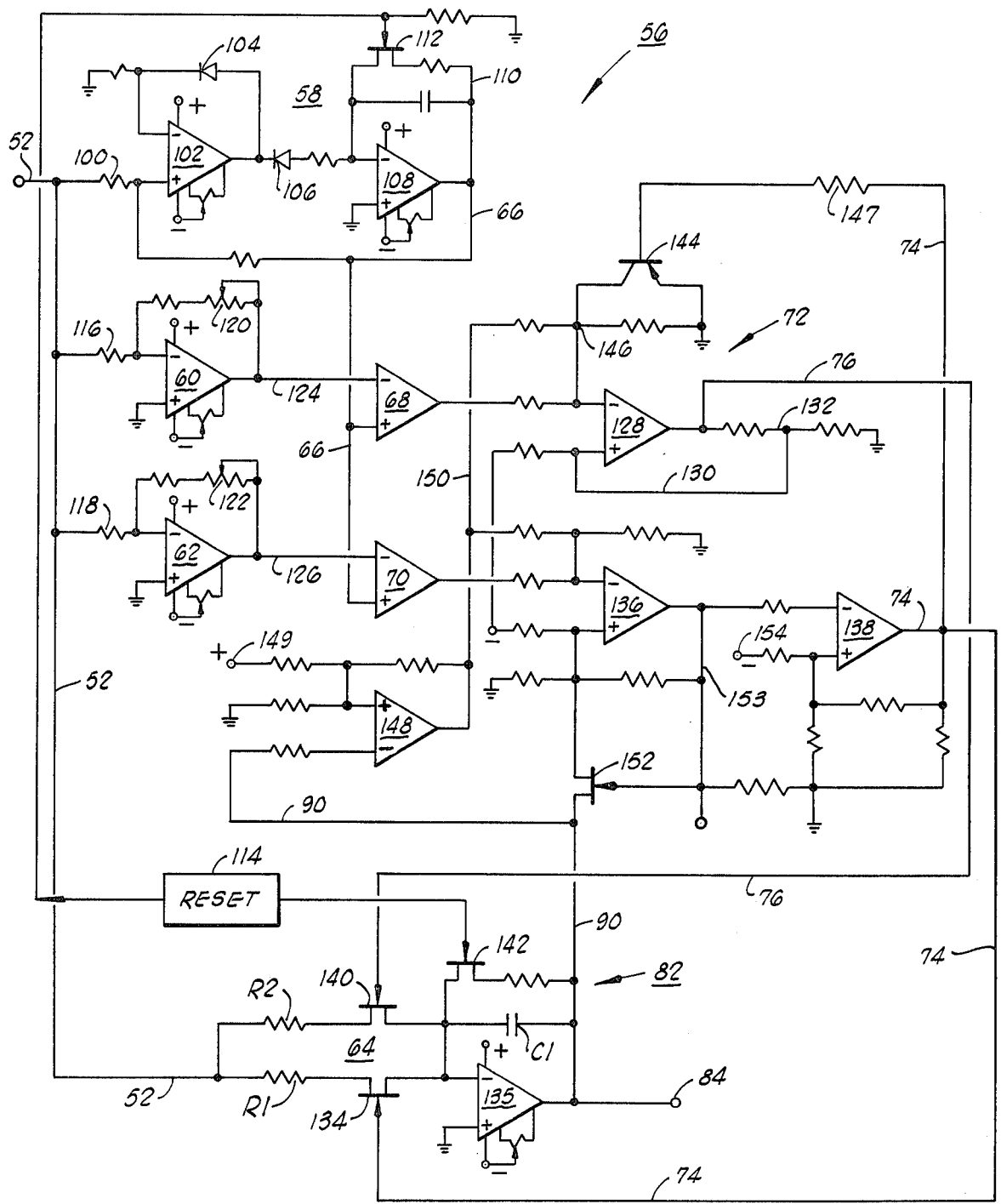
FIG. 3 is a schematic diagram of the circuit of FIG. 1.

FIG. 3 is a schematic diagram of the integration circuitry 56. Accordingly, a time analog curve signal is input at lead 52 for distribution as shown in FIG. 1. The input is applied through a resistor 100 to a plus input of an operational amplifier 102 which constitutes a portion of peak detector 58. The operational amplifier 102 may be such as a standard type 741 integrated circuit op-amp biased in conventional manner with output feedback applied through a diode 104 to the negative input of op-amp 102. Further output through a diode 106 is then applied to the negative input of an op-amp 108, an integrated circuit type 503 functioning as an integrator and the final stage of peak detector 58. Output from integrator 108 is then present on lead 66 for input to comparators 68 and 70. The feedback circuit of integrator 108 is by means of a resistor-capacitor network 110 and a field effect transistor 112, e.g., type 2N5457, which functions during re-set condition in response to actuation of a panel switch or the like indicated generally as re-set 114. Thus, actuation of re-set 114 will serve to cause conduction of FET 112 to return integrator 108 to its zero or base value after an integration procedure.

The concentration curve signal on lead 52 is also applied to the 90 percent amplifier 60 and 33 percent amplifier 62, each of which is an integrated circuit op-amp type 741 with curve signal input provided through respective input resistors 116 and 118 to the respective negative inputs. Cut off calibration is provided by respective feedback potentiometers 120 and 122 from output to input of each amplifier. The respective outputs are then applied via leads 124 and 126 to negative inputs of respective comparators 68 and 70, the peak signal on lead 66 being applied to the respective positive inputs thereof. Comparators 68 and 70 are each constituted of one-quarter section of a type 339 integrated circuit and provide their respective percentage comparator function in full on full off manner to provide control inputs to the interlock logic 72.

Output from the 90 percent comparator 68 is applied to the negative input of a comparator amplifier 128, the positive input being connected via lead 130 and voltage divider resistance network 132 to ground. Amplifier 128 provides output on lead 76 for application to the base of a FET 140 to control application of signal from lead 52 through the integrator R2-C1 for input at the negative input of integration amplifier 135. Output from amplifier 70 is similarly applied to the negative input of a comparator amplifier 136 which, in turn, provides output to the negative input of an inverting amplifier 138. Amplifier 138 provides output via lead 74 to the base of a FET 134, which controls parallel input from lead 52 and enables integrator R1-C1 to the negative input of integrator 82. A FET 142 zeroes integrator 82 in response to actuation of re-set 114 by discharging capacitor C1, whereupon the system is re-set to its zero or restart condition for a next following integration operation. Summation of signals during Phase II takes place at the input of integrator 82 through interaction of resistors R1, R2 and capacitor C1, as will be further described below.

A PNP transistor 144, e.g., type 2N4058, is connected common-emitter with the collector connected to a junction 146 and the negative input to comparator amplifier 128, and base connected via resistor 147 to output lead 74 from comparator amplifier 138. A high level output on lead 74 turns off transistor 144 to assure normal action of the comparator circuitry. Transistor 144 is rendered conductive at the 33 percent level to place a zero voltage on the negative input of comparator amplifier 128. This serves to re-set comparator 128 and cause its output return to a low level. Amplifier 148 receives integral output via lead 90 at its negative input with the positive input supplied by a pre-determined positive reference voltage so that it functions to keep the comparator conditioned with FET 134 conductive and FET 140 open until such time as the integral signal reaches the pre-designated amplitude. A FET 152 receives signal from output lead 153 of comparator amplifier 136 thereby to control application of the integral value output on lead 90 to the positive input of comparator amplifier 136. Negative reference is applied to terminal 154 and the positive input of comparator amplifier 138 to assure reversal of the output of amplifier 138 when the output polarity from amplifier 136 reverses.

Operation of the circuit 56 relies upon the fact that when the selected portion of the true exponential decay curve can be determined, the remaining tailing portion of the curve can be predicted, and will be some constant factor in relation thereto. Hence, the selected sloping portion of the exponential curve, i.e., the portion 18, selected between 90 percent and 33 percent of curve 14 (FIG. 2), can then be integrated and multiplied by a predetermined constant factor to provide a summed area equal to both areas 18 and 20. Standard mathematical procedure provides that the time constant of the exponential portion of the concentration curve as a function of time, $C(t)$, can be found simply by taking the derivative. Once the time constant is established, integration of the total area under the exponential curve portion, area 18 plus area 20 of FIG. 2, establishes that area 20 can be established as a constant portion of total area; that is, having selected the $t_2$ point as 90 percent of curve decay, and with the time constant curve being known, it can be further calculated that the total area under the exponential curve from the 90 percent point through decay is equal to the integrated area 18 times a constant K equal to 1.58. It should be understood that the 90 percent and 33 percent points are arbitrary, and that any two determinant points may be selected with subsequent derivation of the necessary multiplier constant K in accordance with well-known relationships.

Thus, with reference to FIG. 2, concentration curve 14 is integrated from $t_1$ to $t_2$ to provide integral curve value 36; and then further integration of concentration curve 14 from $t_2$ to $t_3$ provides the integral value curve 38 which proceeds as multiplied by constant value 1.58 so that the final integrated value at 28 is obtained after time $t_3$ and is equal to $$\int_{t_1}^{t_2} C(t)dt + 1.58 \int_{t_2}^{t_3} C(t)dt \qquad (2)$$

In circuit operation, the concentration curve input at lead 52 (FIG. 3) is a negative going analog signal and as applied provides the positive going output through peak detector 58 which holds that peak value at output on lead 66 for input to comparators 68 and 70. The negative going concentration curve signal is also applied as input to the 90 percent amplifier 60 and 33 percent amplifier 62, as well as to the integrator circuit 82. The integrator circuit provides an integrated output during the total $t_1$-$t_3$ sweep of curve 14 since FET 134 is closed the entire duration (FIG. 2). Initial closure of FET 134 is assured by the comparator 148 which receives integration indication on lead 90 relative to an established positive reference voltage applied at terminal 149 to maintain output on lead 150 which assures that comparator amplifier 136 through inverter amplifier 138 will maintain an increased voltage or high output for conduction on lead 74 to energize FET 134. Comparator 148 merely functions to keep the comparator conditioned such that FET 134 is closed and FET 140 is open until the integrator signal value at output 84 reaches a preselected amplitude during the $t_1$-$t_2$ duration. In this condition, integration of concentration curve signal on lead 52 is effected by R1 and C1 in conjunction with the operational amplifier 135 to provide the integrated output value at terminal 84.

Time $t_2$ commences when the output from 90 percent amplifier 60 as input to 90 percent comparator 68 reaches a level which is 90 percent of the peak detected input on lead 66 such that comparator 68 goes from high to low output as applied to an input of comparator 128. This input then assures that comparator 128 will reverse to the high output condition wherein lead 76 energizes FET 140 and integration then continues with the additional integration function of R2 and C1 effective. Thus, the 33 percent comparator 70 assures high output to comparator 136 which is driven to a low output controlling inverter amplifier 138 to a high output as applied on lead 74 to maintain FET 134 turned on during $t_2$-$t_3$. Conduction of both FET 140 and 134 brings into play an integrating combination of R1, R2 and C1 so that the output of integrating amplifier 135 adheres to the function $$\frac{1}{\frac{R1 \cdot R2}{R1 + R2} \cdot C} \int C(t)dt \qquad (3)$$

which is $$\frac{R1 + R2}{R1 \cdot R2 \cdot C} \int 0\, C(t)dt \qquad (4)$$

At time $t_3$ all integration is terminated when the output on lead 126 from 33 percent amplifier 62 applies input to 33 percent comparator 70 which is 33 percent of the detected peak value on input 66. At this time, the output from 33 percent comparator 70 goes low, comparator 136 output going high and producing a low output from comparator 138 on lead 74 to open or cut off FET 134. Simultaneously, low output on lead 74 as applied to PNP transistor 144 causes conduction and shorts the negative input of comparator 128 to ground to cause its output to go low which, in turn, provides signal via lead 76 to cut off FET 140. Signal integration is terminated and the output value will hold until re-set 114 is actuated.

To summarize the operation conditions, in the initial condition with FET 142 nonconductive, and with only FET 134 conductive, the integrated output at terminal 84 (value 36 of FIG. 2) is equal to $$\frac{1}{R1 \cdot C1} \int C(t)dt \qquad (5)$$

With FET 142 nonconductive and with both FET 134 and 140 closed, (curved portion 48 of FIG. 2) the output is equal to $$\frac{R1 + R2}{R1 \cdot R2 \cdot C1} \int C(t)dt \qquad (6)$$

With all integrator FET's open after time $t_3$, the output of terminal 84 will hold the last value of the integral and finally, closure of the FET 142 by actuation of re-set 114 will re-set the integrator in preparation of the next cycle or reading.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A circuit for analyzing a time analog concentration curve of the type derived in blood flow analysis in response to introduction of an indicator in the blood system, comprising:

sensing means coactive with the bloodstream for developing an indicator concentration curve in the form of a time analog electrical signal of the type having an initial rise from a base value, through a peak and subsequent exponential decay to said base value;

an input terminal receiving said time analog electrical signal;

a first switching means having input and output;

a first resistance connected between said input terminal and the input to the first switching means;

a second switching means having input and output;

a second resistance connected between said input terminal and the input to said second switching means;

an operational amplifier receiving input from said first and second switching means output;

a capacitor connected from the output of said operational amplifier to said input thereof;

first means receiving input from said operational amplifier and being operative to close said first switching means upon departure of said time analog electrical signal from said base value through initial rise, peak and exponential decay to a first selected value of peak amplitude;

second means including a comparator, receiving input of said time analog electrical signal and being operative to close said second switching means at a second selected value of peak amplitude greater than said first selected value of peak amplitude;

third means including a comparator, receiving input of said time analog electrical signal to open each of said first and second switching means at said first selected value of peak amplitude; and output means receiving output of said operational amplifier to provide an analog voltage indication proportional to the total concentration curve integral.

2. A circuit as set forth in claim 1 which is further characterized to include:

peak detector means receiving said sensed time analog electrical signal and generating a peak signal output for comparator input to said second and third means.

3. A circuit as set forth in claim 2 wherein said peak detector means comprises:

amplifier means receiving input of said time analog electrical signal to provide amplified output;

integrating operational amplifier means receiving said amplified output to provide said peak signal output; and re-set means connected to said integrating operational amplifier and effective to re-set the output thereof to base value.

4. A circuit as set forth in claim 3 which is further characterized to include:

normally open switch means connected between the output and input of said operational amplifier; and re-set means for actuating said switch means and said peak detector re-set means.

5. A circuit as set forth in claim 2 wherein said second means further comprises:

amplifier means receiving input of said time analog electrical signal and generating output at 90 percent of peak signal value; and comparator means receiving input of said peak signal output and said amplifier means output to provide output for effecting closure of said second switching means at 90 percent of said peak signal.

6. A circuit as set forth in claim 2 wherein said third means further comprises:

amplifier means receiving input of said time analog electrical signal and generating output at 33 percent of peak signal value; and comparator means receiving input of said peak signal output and said amplifier means output to provide output for effecting opening of said first and second switching means at 33 percent of said peak signal.

* * * * *